United States Patent [19]

Miyanohara et al.

[11] Patent Number: 4,778,761
[45] Date of Patent: Oct. 18, 1988

[54] RECOMBINANT PLASMID INSERTED WITH HEPATITIS B VIRUS GENE, YEAST TRANSFORMED WITH SAID RECOMBINANT PLASMID, AND PRODUCTION OF HEPATITIS B VIRUS SURFACE ANTIGEN

[75] Inventors: Atsushi Miyanohara, Neyagawa; Chikateru Nozaki; Fukusaburo Hamada, both of Kumamoto; Akio Toh-e, Hiroshima; Nobuya Ohtomo, Kumamoto; Kenichi Matsubara, Osaka, all of Japan

[73] Assignee: Juridical Foundation the Chemosero-Therapeutic Research Institute, Kumamoto, Japan

[21] Appl. No.: 4,424

[22] Filed: Jan. 20, 1987

Related U.S. Application Data

[63] Continuation of Ser. No. 522,705, Aug. 12, 1983, abandoned.

[30] Foreign Application Priority Data

Aug. 16, 1982 [JP] Japan ................ 57-142460

[51] Int. Cl.$^4$ ............. C12N 15/00; C12N 1/00
[52] U.S. Cl. .................... 435/320; 435/68; 435/70; 435/91; 435/172.3; 435/253; 435/255; 435/256; 935/22; 935/23; 935/27; 935/28; 935/29; 935/38; 935/41; 935/56; 935/69; 424/89
[58] Field of Search .............. 435/68, 70, 91, 172.1, 435/172.3, 253, 255, 256, 317, 849, 911; 935/22, 23, 27, 28, 29, 38, 41, 56, 69; 424/88, 89

[56] References Cited

U.S. PATENT DOCUMENTS

| | | | |
|---|---|---|---|
| 4,428,941 | 1/1984 | Galibert et al. | 514/2 |
| 4,446,235 | 5/1984 | Seeburg | 435/91 |
| 4,546,082 | 10/1985 | Kurjan | 435/172.3 |
| 4,615,974 | 10/1986 | Kingsman | 435/68 |

FOREIGN PATENT DOCUMENTS

| | | |
|---|---|---|
| 17682 | 8/1983 | Australia . |
| 0106828 | 4/1984 | European Pat. Off. . |
| 0120551 | 10/1984 | European Pat. Off. . |
| 2034323 | 6/1980 | United Kingdom . |

OTHER PUBLICATIONS

Hitzeman, R. A. et al., Nucleic Acids Research, 11:2745-2763 (9-1983).
Hollenberg, C. P., *Gene Cloning in Organisms Other Than E. Coli*, Springer-Verlag, Berlin (1982), P. H. Hofschneider et al., eds., pp. 119-144, see p. 123.
Botstein, D. et al., *Molecular Biology of the Yeast Saccharomyces*, Cold Spring Harbor Laboratory, N.Y. (1982), J. N. Strathern et al., eds., pp. 607-636, see p. 620.
Dubois, M. F. et al., Proc. Natl. Acad. Sci., U.S.A., 77:4549-4553 (1980).
Valenzuela, P. et al., Nature, 280:815-819 (1979).
Valenzuela, P. et al., Nature, 298:347-350 (1982).
Miyanohara, A. et al., Proc. Natl. Acad. Sci., U.S.A., 80:1-5 (1983).
Charnay, P. et al., Nucleic Acids Research, 7:335-346 (1979).
Charnay, P. et al., Nature, 286:893-895 (1980).
Tiollais, P. et al., Science, 213:406-411 (1981).
Christman, J. K. et al., Proc. Natl. Acad. Sci., U.S.A., 79:1815-19 (3-1982).
Beggs, J. D., Nature 275: 104-109 (1978).
Beggs, J. D. et al., Nature 283:835-840 (1980).
Fraser, T. H. et al., *Microbiology*-1981, Genetech Inc., CA. (1981), pp. 392-395.
R. A. Hitzeman et al., Expression of a Human Gene for Interferon in Yeast, Nature, vol. 293, pp. 717-722, (1981).
B. Meyhack et al., Two Yeast Acid Phosphatase Structural Genes are the Result of a Tandem Duplication and Show Different Degrees of Homology in their Promoter and Coding Sequences, The Embo Journal, vol. 1, No. 6, pp. 675-680, (1982).
J. Ferguson et al., Construction and Characterization of Three Yeast *Escherichia Coli* Shuttle Vectors Designed for Rapid Subcloning of Yeast Genes on Small DNA Fragments, Gene, 16, pp. 191-197, (1981).
H. Rudolph et al., The Yeast PHO5 Promoter: Phosphate-Control Elements and Sequences Mediating mRNA Start-Site Selection, Proc. Natl. Acad. Sci., U.S.A., vol. 84, pp. 1340-1344, (1987).
P. Valenzuela et al., Nature, vol. 298, pp. 347-350, (1982).
K. Arima et al., The Nucleotide Sequence of the Yeast PHO5 Gene: A Putative Precursor of Repressible Acid Phosphatase Contains a Signal Peptide, Nucleic Acids Research, vol. 11, No. 6, pp. 1657-1672, (1983).

*Primary Examiner*—Margaret Moskowitz
*Attorney, Agent, or Firm*—Wegner & Bretschneider

[57] ABSTRACT

A recombinant plasmid inserted with Hepatitis B virus gene, which comprises a plasmid vector containing a yeast gene and an *E. coli* gene and carrying the expression control region of the repressible acid phosphatase gene of yeast and a Hepatitis B virus gene recombined thereto under control of the phosphatase promoter, a transformed yeast which is prepared by transforming a yeast with the recombinant plasmid, and a method of the production of Hepatitis B virus surface antigen in a large scale by culturing the transformed yeast in a medium. The Hepatitis B virus surface antigen prepared by the present invention has the same immunological properties as those of the natural antigen from human blood plasma and is useful for the preparation of Hepatitis B virus vaccine and diagnostic reagents.

2 Claims, No Drawings

RECOMBINANT PLASMID INSERTED WITH HEPATITIS B VIRUS GENE, YEAST TRANSFORMED WITH SAID RECOMBINANT PLASMID, AND PRODUCTION OF HEPATITIS B VIRUS SURFACE ANTIGEN

This application is a continuation of Ser. No. 522,705, filed Aug. 12, 1983 now abandoned.

BACKGROUND OF THE INVENTION

The present invention relates to a novel recombinant plasmid inserted with a Hepatitis B virus gene, an yeast transformed with the plasmid, and a method for the production of Hepatitis B virus surface antigen. More particularly, it relates to a recombinant plasmid which is obtained by inserting Hepatitis B virus (HBV) surface antigen (hereinafter, referred to as "HBs antigen", "HBsAg" or "s antigen") gene into a shuttle vector which can replicate in both *Escherichia coli* and yeast at downstream of the expression control region of the repressible acid phosphatase gene (said region being hereinafter referred to as "acid phosphatase promoter" or "acid phosphatase gene") carried on the vector, an yeast transformed with said recombinant plasmid, and a method for the production of an immunologically active HBs antigen (HBsAg) comprising culturing said transformed yeast in an appropriate medium under the conditions that the acid phosphatase promoter is not repressed.

Hepatitis B which is usually caused by transfusing blood of HBV positive patient or others is hardly remedied, and there is no drug suitable for complete remedy thereof. Most suitable prophylaxis is a vaccine consisting of HBs antigen. However, it is very difficult to produce the HBsAg vaccine in an industrial scale, because HBV is infectious only to human subjects and chimpanzee (it has never been succeeded to make cell culture infected with HBV), and owing to this specificity of HBV, HBsAg must be obtained only from human blood serum.

It has recently been proposed to prepare HBsAg by *E. coli* with a recombinant DNA instead of using human blood serum (cf. Japanese Patent Laid Open Application No. 104887/1980). However, according to this method using *E. coli*, it is still difficult to produce the desired HBsAg in an industrial scale, because the produced HBsAg is easily decomposed within the cells of *E. coli* and further growth of *E. coli* is inhibited by the HBsAg produced, which results in less productivity of HBsAg.

It has very recently been reported that HBs antigen particles have successively been produced by an yeast [cf. Nature, 298, 347–350 (22 July, 1982)]. It is described in this report to recombine a gene encoding an HBs protein to an *E. coli*-yeast shuttle vector at downstream of an alcohol dehydrogenase I (ADH1) promoter which is usually used in the production of interferone by yeast. According to this method, however, the amount of HBs protein is so small, and hence, it is not satisfactory to produce the desired HBs antigen in an industrial scale.

The present inventors have extensively studied on an improved method for producing HBsAg in an industrial scale. As a result, it has been found that the desired HBsAg can be produced in a large scale by recombining a gene of HBs antigen to a specific plasmid vector having an yeast gene and *E. coli* gene and carrying the repressible acid phosphatase gene of the yeast including the phosphatase promoter, transforming an yeast with the recombinant DNA thus obtained, and culturing the transformed yeast, and that the HBsAg thus obtained has the same immunological properties as those of HBsAg originated from human blood plasma.

An object of the present invention is to provide a novel recombinant plasmid inserted with an HBs antigen gene. Another object of the invention is to provide a transformed yeast which is produced by transforming an yeast with the novel recombinant plasmid as set forth above. A further object of the invention is to provide a method for production of HBsAg in an industrial scale. These and other objects and advantages of the invention will be apparent to persons skilled in the art from the following description.

The recombinant plasmid inserted with an HBV gene of the present invention is obtained by utilizing a shuttle vector which has both *E. coli* gene and yeast gene and can replicate in both of them, and by recombining an HBs antigen gene into the vector to downstream of the acid phosphatase promoter carried on the vector wherein a part or whole of the structural gene of the acid phosphatase or a certain region of upstream of the phosphatase structural gene are preferably deleted. The transformed yeast is prepared by transforming an yeast with the thus obtained plasmid which expresses HBs gene by a conventional method. The desired HBs protein can be produced by culturing the transformed yeast in an appropriate medium, preferably under the conditions that the acidic phosphatase promoter is not repressed.

BRIEF DESCRIPTION OF THE DRAWINGS

FIG. 1 is a diagrammatic chart of HBV DNA genome of subtype adr showing restriction enzyme recognition sites.

FIG. 2 shows the DNA nucleotide sequence of HBs gene component of HBV.

FIG. 3 is a diagrammatic representation of shuttle vector pAT77 and illustrates the steps in the manufacture of shuttle vector pAM82.

FIG. 4 is a diagrammatic gene map of the acidic phosphatase structural gene region.

FIG. 5 shows the DNA nucleotide sequence of Bst EII-sal I restriction site of the shuttle vector pAT77.

FIG. 6 is a graph of RIA test results comparing HBsAg produced by the present invention to a control sample.

DETAILED DESCRIPTION OF THE INVENTION

The recombinant plasmid, transformed yeast and production HBsAg with the transformed yeast will be illustrated below in more detail.

(1) HBV gene

The HBV gene to be inserted into the shuttle vector is an HBV DNA of subtype adr which is frequently observed in Japan and also in countries of Southeast Asia and is cloned by *E. coli*. The HBV DNA contains each one recognition site of restriction enzymes Xho I and BamHI. This fragment, e.g. a fragment having a Xho I site at the terminal which is obtained by digesting with Xho I has a structure as shown in the accompanying FIG. 1, wherein HBs gene and HBc gene are present in the same direction.

As is shown in FIG. 1, the HBs coding sequence initiates 28th nucleotide from the 5'-end when cleaved with Xho I and contains a nucleotide sequence corresponding to 226 amino acids and also an HBc gene downstream thereof in the same direction. When this fragment of the HBs gene (HBV DNA of 3.2 kb) is treated with BamHI, it is divided into a fragment (about 1.3 kb) containing an HBs gene and a fragment (about 1.9 kb) containing an HBc gene. The nucleotide sequence of this HBs gene has been determined by the present inventors and is as shown in the accompanying FIG. 2. (the DNA sequence of the gene of HBV of subtype of adw which is frequently observed in European countries and U.S.A. is already known) Both of the HBs gene and HBc gene do not have any intervening sequence. In FIG. 2, the upper line means a nucleotide sequence of a region for determining "s" antigen and the second line means an amino acid sequence encoded thereby, and the number marked upper the nucleotide sequence means a nunber of amino acids counted from the N-terminal of the "s" antigen. The three lines below means respectively the data of ad/yw type (analyzed by Pasek et al, Nature, 282, 575–579, 1979), adw type (analyzed by Valenzuela et al, Nature, 280, 815–819, 1979) and ayw type (analyzed by Charnay et al, Proc. Natl. Acad. Sci., U.S.A., 76, 2222–2226, 1979).

The HBV DNA is prepared in the following manner.

Viral particles (Dane particles) are isolated from blood of a person having an HBe antigen by a conventional method. The HBV DNA (3,200 bp) has usually a double-stranded circular structure, but about 15 to 50% regions thereof are single-strand. Accordingly, in order to change the single-stranded regions to double-strand suitable for cloning the gene, it is treated with an endogenous DNA polymerase by a method of Sattler and Robinson (cf. F. Sattler and W. S. Robinson, Journal of Virology, 32, 226–233, 1979, "Hepatitis B viral DNA molecules have cohesive ends"). After repairing all regions into double-strand, the DNA is extracted, and amplified by cloning by E. coli, and then treated with an appropriate restriction enzyme to give a fragment which is used for construction of the desired plasmid.

The HBV DNA is preferably of subtype adr which is frequently observed in Japan and in other countries in Southeast Asia, but may be HBV of subtype adw and ayw which are frequently observed in European countries and U.S.A.

(2) Shuttle vector

The shuttle vector used in the present invention is a plasmid vector which contains both of yeast gene and E. coli gene and carries the repressible acid phosphatase gene of the yeast, e.g., Saccharomyces cerevisiae.

The yeast gene usually contains a DNA sequence which is necessary for replication of a plasmid in the yeast independently from chromosome, for instance, a DNA sequence necessary for the autonomous replication of the yeast (which is designated "ars 1"), and a DNA sequence necessary for the replication of 2 μm DNA (which is designated "2μ ori"), and contains optionally a gene useful as a selective marker of the transformed yeast. The selective marker includes, for example, a leucine-producing gene, a histidine-producing gene, a tryptophane-producing gene, a uracil-producing gene, an adenine-producing gene, or the like, which may be used alone or in combination of two or more thereof.

The E. coli gene contains a DNA sequence necessary for the replication of the plasmid within cells of E. coli, for example, a DNA sequence of a replication initiating region of plasmid of Col EI, and preferably contains a gene useful as a selective marker of the transformed E. coli. The selective marker includes, for example, an ampicillin-resistant gene, a kanamycin-resistant gene, tetracycline-resistant gene, chloramphenicol-resistant gene, or the like, which may be used alone or in combination of two or more thereof. Commonly used E. coli DNA is pBR322 which contains an ampicillin-resistant gene and a tetracycline-resistant gene.

The shuttle vector used in the present invention is characteristic in that it carries the repressible acid phosphatase promoter of the yeast. This acid phosphatase promoter is usually a promoter of polypeptide of 60,000 dalton (P60) which constitutes the phosphate.

Representative example of the shuttle vector is a shuttle vector which is prepared by the present inventors by recombining an yeast DNA containing ars 1, 2μ ori and a leucine-producing gene (Leu 2) as a gene of yeast with an E. coli plasmid pBr322. The shuttle vector is designated "pAt 77" and is prepared as follows.

An EcoRI fragment of about 8,000 nucelotide pair (8 kb) containing a polypeptide (P60) gene of 60,000 dalton which constitutes the repressible acid phosphatase (cf. PNAS, 77, 6541–6545, 1980, and PNAS, 79, 2157–2161, 1982) is inserted into the EcoRI site of known E. coli plasmid pBR322 (cf. Sutcliffe, J. G.; Cold Spring Harbor Symposium, 43, 77–90, 1979) to give a plasmid, which is used as the starting material. Said EcoRI fragment (8 kb DNA fragment) contains a single recognition site of a restriction enzyme Sal I at the position of dividing into about 2.8 kb and about 5.2 kb wherein an ampicillin-resistant gene of pBR322 locating in the fragment of about 2.8 kb.

The starting plasmid is digested with a restriction enzyme Sal I and re-annealed with T4 DNA ligase to give a plasmid which is deficient from the Sal I site to the acid phosphates gene fragment 5.2 kb (said plasmid being designated "pAT 25"). Said pAT 25 is a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof.

Into the EcoRI site of the above pAT 25 is inserted an EcoRI fragment (1.4 kb) containing a DNA sequence necessary for the autonomous replication of the yeast (ars 1) and a Trp 1 gene of yeast (cf. PNAS, 76, 1035–1039, 1979) to give a plasmid (designated "pAT 26"). Said ars 1-Trp 1 fragment has a single recognition site of a restriction enzyme Hind III within the Trp 1 gene.

Into the Hind III site of the above pAT 26 is inserted a Hind III fragment containing a leucine-producing gene of yeast (Leu 2) and a DNA sequence necessary for the replication of 2 μm DNA (2μ ori) (cf. Tohe, A., Guerry, p., Wichener, R. B.; J. Bacteriol., 141, 413–416, 1980) to give the desired shuttle vector pAT 77.

The pAT 77 and pAM 82 derived therefrom as described hereinafter have the structures as shown in the accompanying FIG. 3. In FIG. 3, the thick line region is the gene originated from E. coli plasmid pBR322 and the remainder region is the gene of yeast. More specifically, the pAT 77 contains a fragment of from EcoRI site up to Sal I site containing ampicillin-resistant gene (Ap$^r$) of pBR 322 as the E. coli gene and a fragment of from EcoRI site linked with pBr 322 up to Sal I site through ars 1, 2μ ori and Leu 2 genes in this order and further upstream of the acid phosphatase gene, wherein the *E. coli* gene and the yeast gene link at EcoRI site and Sal I site. This pAT 77 can replicate in *E. coli* cells because of presence of pBR322 gene and can also replicate in yeast because of presence of ars 1 and 2μ ori genes. Moreover, this plasmid contains as the selective marker for transformant an ampicillin-resistant gene (Ap$^r$) at the side of *E. coli* and a leucine-producing gene (Leu 2) at the side of yeast, and hence, has satisfactory properties as a shuttle vector.

The shuttle vector is required for preparing the recombinant plasmid by using *E. coli*, and when an yeast is transformed with the recombinant plasmid, the *E. coli* gene is not necessary but may be deleted therefrom.

The gene map around the acid phosphatase promoter of the shuttle vector pAT 77 is shown in the accompanying FIG. 4. The nucleotide sequence of BstEII-Sal I region in this shuttle vector has been determined by the present inventors and is as shown in the accompanying FIG. 5. The ATG codon (methionine) shown in FIGS. 4 and 5 is the initiator codon of the acid phosphatase. More specifically, the repressible acid phosphatase gene fragment (about 2.8 kb) of this vector contains the region covering from about 2.7 kb upstream from the structural gene to 82nd nucleotide pair (82 bp) of the structural gene.

The shuttle vector pAT 77 is cleaved by treating with a restriction enzyme Sal I, followed by treating with an exonuclease BAL 31, by which a part or whole of the structural gene of acid phosphatase as shown in FIGS. 4 and 5 and further optionally various regions upstream therefrom are deleted. This deletion is effected for appropriate regions before the acid phosphatase promoter region: TATATAA (hogness box), i.e. −100 bp. The regions to be deleted can be controlled by the conditions for treating with the exonuclease and are usually in the range of from +1 to −100 bp, preferably from +1 to −50 bp. When the deletion is effected too wide range of upstream, i.e. over −100 bp, it becomes to be difficult to control the acid phosphatase promoter, which results in lowering of yield of the desired HBsAg in the culture of the transformed yeast cells. On the other hand, when the deletion is insufficiently effected so that a part of the acid phosphatase structural gene is remained, a mulatto of the HBs antigen and a phosphatase peptide is disadvantageously produced.

After deleting a part of whole of the acid phosphatase structural gene and optionally some regions upstream therefrom, a synthetic or natural linker, for example Sal I linker or Xho I linker, is recombined thereto to give a circular plasmid, by which there is obtained a shuttle vector which can express an alien gene in the pure form under control of the acid phosphatase promoter. This shuttle vector can readily be cleaved at the site to be recombined by treating with a conventional restriction enzyme, such as Sal I or Xho I, and hence, is preferably used in order to recombine with the desired gene.

(3) Construction of HBs gene-expression plasmid

The recombinant plasmid of the present invention, i.e. a plasmid recombined with an HBs gene, is prepared by cleaving the above shuttle vector with a restriction enzyme responding to the used linker, for example, Sal I or Xho I, and then recombining the resulting cleaved fragment with the HBV DNA as mentioned hereinbefore. The plasmids thus obtained are amplified by *E. coli*, and only the desired plasmid which is recombined in the correct direction is selected by analyzing with digestion by restriction enzymes, Xho I or Sal I (insertion), EcoRI and Xho I (direction of insertion).

(4) Transformation of yeast

The yeast to be transformed includes a mutant strain of yeast which is complemental with the selective marker gene of the transformed yeast carried on the plasmid, for example, a leucine-requiring mutant, *Saccharomyces cerevisiae* AH22 [a, leu 2, his 4, Can 1 (Cir+)] (cf. Hinnen, A. et al, Proc. Natl. Acad. Sci, U.S.A., 75, 2157–2161, 1978). After amplifying by *E. Coli*, the recombinant plasmid is applied to the mutant strain of yeast in a usual manner, for example, by mixing the plasmid DNA with cells obtained by converting into spheroplast, followed by treating with calcium, by which the transformation is effected. The desired transformed yeast is selected and isolated from the yeast culture thus treated based on the expression of a gene complemental with the mutation of the host yeast carried on the vector, for example, expression of a leucine-producing gene.

In addition to the above-mentioned leucine-requiring strain, various other mutant strains such as a histidine-requiring strain, tryptophane-requiring strain, uracil-requiring strain, adenine-requiring strain, or the like can be used as the yeast. One Example of other strain is *S. cerevisiae* SHY3 (a, ste-VC9, ura 3, trp 1, leu 2, his 3, ade 1, can 1).

(5) Culture transformed yeast and production of HBsAg

The transformed yeast obtained above is cultured in a medium containing phosphoric acid in a usual manner, and the culture cells in logarithmic growth phase are transferred to an inorganic phosphate free medium and then are cultured under a condition that the acid phosphatase promoter is not repressed. After the culture, the produced cells are collected and lysed in a usual manner to give a lysed cell solution containing a large amount of the desired HBsAg.

Depending on the kind of an yeast, for instance, when Pho 80 mutant strain (cf. Thoe, A. et al, J. Bacteriol., 145, 221–232, 1981) is used, the culture is not necessarily required to be carried out under the condition that the acid phosphatase promoter is not repressed, but may be done under a usual condition to give directly the desired HBsAg in a large amount.

The HBsAg thus obtained is the same as the natural HBsAg originated from human blood plasma in terms of immunological properties, and hence, is useful for the preparation of HBV vaccine like the HBsAg from human blood plasma.

The present invention is illustrated by the following Example but should not be construed to be limited thereto.

EXAMPLE 1

(1) Preparation of HBV DNA (i) Preparation of virus DNA

A pooled blood plasma (700 ml) obtained from ten persons who are positive in HBsAg (subtype adr) and HBeAg is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (pH 7.5) of 10 mM Tris-HCl, 0.1M NaCl and 1 mM EDTA. The solution is added to the top of a centrifugal tube containing 30% sucrose, which is centrifuged at 4° C., 39,000 r.p.m. for 4 hours. The resultant precipitates are re-dissolved in the same buffer as above.

In order to make easier the following operation, the buffer solution is subjected to the reaction by HBV DNA polymerase by treating it in a mixture (500 μl) of 67 mM Tris-HCl (pH 7.5), 80 mM NH$_4$Cl, 25 mM MgCl$_2$, 0.5% NP40 (tergitol, manufactured by Sigma Co.), 0.1% 2-mercaptoethanol, 330 μM dCTP (deoxycytidine triphosphate), dGTP (deoxyguanisine triphosphate), and dATP (deoxyadenosine triphosphate), 0.5 μM α-[=P]dTTP (deoxythymidine triphosphate) at 37° C. for 3 hours, and to the reaction mixture is added the same volume of 100 mM EDTA solution. By the above DNA polymerase reaction, single-stranded region of the DNA is repaired to wholly double-strand to give a [$^{32}$P] labeled material. This material is added to the top of a centrifugal tube wherein 30%, 20% and 10% aqueous solutions of sucrose are packed in layers in this order, and it is centrifuged at 4° C., 39,000 r.p.m. for 4.5 hours.

In order to digest the proteins strongly bonded to DNA, the precipitates obtained above are treated in a mixture (200 μl) of 1 mg/ml of pronase E (manufactured by Kaken Kagaku K.K.) and 0.2% aqueous sodium lauryl sulfate solution at 37° C. for 2 hours. The resulting mixture is extracted with phenol (200 μl) twice, and the resulting DNA-containing extract is washed with ether to remove phenol solvent to give a solution of HBV DNA. The DNA thus obtained has a specific radioactivity of $2.5 \times 10^6$ cpm/μg and can be used for digestion with restriction enzymes.

(ii) Cloning of HBV DNA

The double-stranded circular HBV DNA obtained above is cloned by using λ-phage Sharon 16A DNA as a vector and then is again cloned by using the known plasmid pACYC177 as a vector as follows.

(A) Cloning in the system of λ-phage Sharon 16A host-vector:

HBV DNA (20 ng) is treated with endonuclease Xho I in a mixture (20 μl) of 10 mM Tris-HCl (pH 7.4), 7 mM MgCl$_2$, 100 mM NaCl and 7 mM 2-mercaptoethanol at 37° C. for 2 hours. The resulting mixture is extracted with phenol (20 μl) and further with ether, and to the aqueous layer is added a double volume of cooled ethanol to precipitate DNA. The mixture is kept at −70° C. for one hour and then centrifuged at 10,000 r.p.m. for 5 minutes, and the precipitated DNA is recovered. The precipitates thus separated are dissolved in a mixture (5 μl) of 10 mM Tris-HCl (pH 7.4) and 1 mM EDTA. The HBV DNA and an equimolar amount of λ-phage Sharon 16 A DNA (having one recognition site of Xho I) obtained by cleavage with endonuclease Xho I in the same manner as above are reacted with T4 DNA ligase [a mixture of 50 mM Tris-HCl (pH 7.4), 10 mM MgCl$_2$, 10 mM dithiothreitol, 100 μl/ml calf serum albumin, 0.5 mM ATP and 0.5 μl enzyme preparation (T4 ligase, manufactured by Takara biomedicals, $1-5 \times 10^3$ unit/ml)] at 4° C. for 18 hours. The reaction mixture is extracted with phenol and ether and then subjected to precipitation with ethanol in the same manner as described above. The precipitates thus obtained are dissolved in a mixture (10 μl) of 10 mM Tris-HCl (pH 7.4) and 1 mM EDTA.

The thus annealed DNA is subjected to in vitro packaging operation to form λ-phage in the same manner as described in "Methods in Enzymology", 68, 299–309 and further plaques (10$^4$) are formed therefrom on an L-agar plate (23 cm×23 cm) by using E. coli DP50 SupF (cf. Blattner, F. R. et al, Science 196, 161, 1977) as an indicator. These plaques are subjected to plaque hybridization using $^{32}$P-labeled HBV DNA prepared above as a probe (cf. Science, 196, 180, 1977) in order to select plaques formed from the phage having HBV DNA, by which a plural of the desired phages are separated.

(B) Re-cloning by using plasmid pACYC177 as a vector:

From the phage having HBV DNA obtained in the above (A), a phage DNA is prepared by using E. coli DP50-SupF as a bacteria to be infected in the same manner as described in "Methods in Enzymology", 68, 245–378, 1979. The DNA thus obtained is digested with Xho I under the same conditions as described above for 2 hours, and the resulting reaction mixture is subjected to an electrophoresis with 0.75% agarose gel to isolate HBV DNA (3.2 kb). The HBV DNA is absorbed onto DEAE (diethylaminoethyl cellulose) paper (manufactured by Toyo Roshi, Japan) in order to separate from the vector DNA and then eluted with 1M NaCl aqueous solution to give an HBV DNA having Xho I terminals at both ends.

Separately, plasmid pACYC177 (cf. Chang, A. C. Y., Cohen, S. N.; J. Bacteriol., 134, 1141–1156, 1978) having a single Xho I cleavage site within kanamycin-resistant gene thereof is digested with Xho I, and the product is purified by phenol extraction, ether treatment and ethanol precipitation in the same manner as described above.

The thus obtained pACYC177 cleaved with Xho I is mixed with XhoI-terminal HBV DNA obtained above in a molar ratio of 1:5, and the mixture is annealed with T$_4$ DNA ligase for 18 hours as described above.

The annealed DNA preparation (10 μl) obtained above is added to a liquid of E. coli (0.1 ml) which is prepared by treating a culture broth of E. coli χ1776 [cf. R. III. Curtiss, et al, "Molecular cloning of recombinant DNA" eds. W. A. Scott and R. Werner, page 99, Academie Press (1977)] by the procedure as described in M. V. Norgard, Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml) and is incubated at 37° C. overnight. The resulting colonies are applied onto both an agar plate containing kanamycin (20 μg/ml) and an agar plate containing ampicillin (20 μg/ml), and the colonies which grow only on the agar plate containing ampicillin is selected. pACYC177 has an ampicillin-resistant gene and a kanamycin-resistant gene, but when it is inserted with HBV DNA at the Xho I site of the kanamycin-resistant gene, it looses the kanamycin-resistance. Accordingly, the selected colonies have a recombinant DNA of pACYC177-HBV DNA. From the colonies thus selected, a plasmid is prepared by the procedure as described by K. Matsubara (J. Virol., 16, 479, 1975). The plasmid thus obtained, i.e. the recombinant DNA of pACYC177-HBV DNA (which is designated "pHBV"), is treated with Xho I under the same conditions as described above to give total HBV DNA fragment (3.2 kb). Besides, when it is treated with Xho I and BamHI, there is obtained a fragment (about 1.3 kb) containing an HBsAg gene.

(2) Preparation of shuttle vectors pAM81, 82, 83 and 84

An EcoRI fragment of about 8,000 nucleotide pair (8 kb) containing a polypeptide (P60) gene of 60,000 dalton which constitutes the repressible acid phosphatase (available from Yeast S288C gene bank, Clarke, L. and Carbon, J., Cell, 9, 91–99, 1976) is inserted into the EcoRI site of known E. coli plasmid pBR322 to give a plasmid, which is used as the starting material.

The starting plasmid is digested with a restriction exzyme Sal I and re-annealed with T4 DNA ligase to give a plasmid pAT25 which is deficient from the Sal I site to the acid phosphatase gene fragment 5.2 kb [said plasmid pAT 25 being a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof].

Into the EcoRI site of the above pAT 25 is inserted an EcoRI fragment (1.4 kb) containing ars 1 and Trp 1 gene which is prepared by treating a plasmid YRP 7 (cf. Struhl, K. et al, Proc. Natl. Acad. Sci. U.S.A., 76, 1035–1039, 1979) with EcoRI to give a plasmid pAT 26. Said ars 1-Trp 1 fragment has a single recognition site of a restriction enzyme Hind III within the Trp 1 gene.

Into the Hind III site of the above pAT 26 is inserted a Hind III fragment containing a Leu 2 and 2µ ori which is prepared by treating a plasmid pSLE 1 (cf. Tohe, A. et al, J. Bacteriol., 141, 413–416, 1980) with Hind III to give the desired shuttle vector pAT 77. The pAT 77 carried on *Saccharomyces cerevisiae* (i.e. *Saccharomyces cerevisiae* AH 22/pAT 77) has been deposited at Fermentation Research Institute, Agency of Industrial Science and Technology, Japan under Budapest Treaty as "FERM BP-324".

The pAT 77 thus obtained (1 µg) is cleaved with Sal I and then is treated with an exonuclease BAL 31 (0.1 U) in a solution (50 µl) of 20 mM Tris-HCl (pH 8.2), 12 mM CaCl$_2$, 12 mM MgCl$_2$, 0.2M NaCl and 1 mM EDTA for 30 seconds to one minute. The reaction mixture is subjected to phenol extraction and ethanol precipitation in the same manner as described above. The resulting precipitates are treated with Xho I linker (1 pmol) and T4 DNA ligase under the same conditions as described above for 12 hours.

*E. coli* χ1776 is treated with the above reaction mixture by the procedure as described in R. III. Curtiss et al, "Molecular cloning of recombinant DNA" eds. W. A. Scott and R. Werner, page 99, Academic Press (1977) so as to transform the *E. coli* χ1776 to give an ampicillin-resistant transformant. From the resulting transformant colonies, plasmid DNAs are prepared by the procedure as described by K. Matsubara (j. Virol., 16, 479, 1975). According to Maxam-Gilbert method (cf. Maxam, A. and Gilbert, W.; Pro. N.A.S., 74, 560–564), the nucleotide sequence of the resulting DNAs is determined, and further, the region of the acid phosphatase gene deleted with BAL 31 is determined. Among these DNAs, the desired plasmids pAM 81, pAM 82, pAM 83 and pAM 84 which are completely deficient in whole of the structural gene of phosphatase are selected and isolated.

Designating "A" in the carbon ATG encoding the first amino acid (methionine) of the product P60 of the phosphatase structural gene as "+1", the following regions are deleted in these shuttle vectors, pAM 81: till +2, pAM 82: till −33, pAM 83: till −50, and pAM 84: till −51. The pAM 81, pAM 82, pAM 83 and pAM 84 carried on *Saccharomyces cerevisiae* (i.e. *Saccharomyces cerevisiae* AH 22/pAM 81, AH 22/pAM 82, AH 22/pAM 83 and AH 22/pAM 84, respectively) have been deposited at Fermentation Research Institute, Agency of Industrial Science and Technology, Japan under Budapest Treaty as "FERM BP-325", "FERM BP-313", "FERM BP-327", and "FERM BP-326", respectively.

(3) Preparation of HBsAg gene-expression plasmids (i) Preparation of plasmids inserted with whole of HBV DNA HBV DNA obtained by treating a plasmid pHBV (pACYC 177-HBV DNA) with Xho I is recombined with Xho I cleaved shuttle vector, pAM 81, pAM 82, pAM 83 and pAM 84 in the molar ratio of 5:1 by annealing with T4 DNA ligase under the same conditions as described above.

*E. coli* χ1776 is transformed with the reaction mixture and a plasmid DNA is prepared from the resulting ampicillin-resistant transformant in the same manner as described hereinbefore. The DNAs thus prepared are analyzed with various restriction enzymes, such as Xho I, Xba I and Hind III, and thereby, insertion of HBV DNA into the vectors and direction thereof are determined.

The thus obtained HBsAg gene-expression plasmids have HBs gene and HBc gene in this order downstream the phosphatase promoter, and the plasmids recombined with the shuttle vectors, pAM 81, pAM 82, pAM 83 and pAM 84 are designated pAH 201, pAH 203, pAH 205 and pAH 207, respectively.

(ii) Preparation of plasmid inserted with HBsAg gene fragment

An HBsAg gene fragment (3 µg) prepared by cleaving plasmid pHBV with BamHI is treated with T4 DNA polymerase (0.2 U) in a solution (100 µl) of 67 mM Tris-HCl (pH 8.6), 6.7 mM MgCl$_2$, 10 mM 2-mercaptoethanol, 6.7 µM EDTA and 16.7 mM (NH$_4$)$_2$SO$_4$ which contains 200 µM αATP, αCTP, αTTP and αGTP for 30 minutes in order to fill-in the BamHI cleavage end. The reaction mixture is subjected to phenol extraction and ethanol precipitation as described above. The resulting precipitates are subjected to linking reaction with Xho I linker in a molar ratio of 1:10 with T4 DNA ligase under the same conditions as described hereinbefore. After phenol extraction and ethanol precipitation, the resulting plasmid is treated with Xho I to give an HBsAg gene fragment (about 1.3 kb) having Xho I cleavage terminal at both ends. The fragment thus obtained is annealed with the shuttle vector pAM 82 which is cleaved with Xho I in a molar ratio of 5:1 by using T4 DNA ligase, and *E. coli* χ1776 is transformed with the reaction mixture obtained above in the same manner as described in the above (i) to give a plasmid DNA.

The plasmid thus obtained is inserted with HBsAg gene in a correct direction downstream the phosphatase promoter of the vector pAM 82, which plasmid is designated pAS 101.

(4) Preparation of transformed yeast

The starting yeast is *Saccharomyces cerevisiae* AH22 [a, leu2, his4, can1 (Cir+)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2%R glucose, and the mixture is incubated at 30° C. overnight, and thereafter, the cells are collected by centrifugation. The cells thus collected are washed with sterilized water (20 ml), suspended in a solution (5 ml) of 1.2M sorbitol and 100 µg/ml zymolyase-60,000 (manufactured by Seikagaku Kogyo K.K., Japan), and the suspension is allowed to stand at 30° C. for 30 minutes to give spheroplast. The spheroplast thus prepared is washed with 1.2M sorbitol solution three times, and then suspended in a solution (0.6 ml) of 2M sorbitol, 10 mM CaCl₂ and 10 mM Tris-HCl (pH 7.5). The suspension thus prepared is divided into a small test tube in a volume of 60 μl. To the suspension is added the solution of the recombinant plasmid pAH 203 (30 μl) prepared in the above (3). After mixing well, 0.1M CaCl₂ (3 μl) is added thereto in a final concentration of 10 mM CaCl₂, and the mixture is allowed to stand at room temperature for 5 to 10 minutes. To the resulting mixture is added each 1 ml of a solution of 20% polyethylene glycol 4,000, 10 mM CaCl₂ and 10 mM Tris-HCl (pH 7.5), and the mixture is allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 μg/ml histidine and 3% agar, which is kept at a constant temperature of 45° C. After gentle mixing, the mixture is added in a layer onto a plate of minimal medium containing 1.2M sorbitol which is previously prepared and consists of 0.7% yeast nitrogen base amino acid, 2% glucose, 20 μg/ml histidine and S2% agar and is set thereon. The plate is incubated at 30° C. to give a colonie of a leucine-non-requiring yeast. The colonie is incubated in a BurkHolder minimal medium supplemented with histidine (20 μg/ml) [cf. Tohe, A. et al; J. Bachterol., 113, 727-738, 1973] to give the desired transformed yeast: Saccharomyces cerevisiae pAH 203.

In the same manner as described above, except that the recombinant plasmids, PAS 101, pAH 201 and pAH 205 are used instead of the recombinant pAH 203, the following transformed yeasts are prepared:

Saccharomyces cerevisiae pAS 101
Saccharomyces cerevisiae pAH 201
Saccharomyces cerevisiae pAH 205

(5) Production of HBsAg with the transformed yeast

Each colonie of the transformed yeasts obtained in the above (4) is applied onto an agar plate of Burk-Holder minimal medium supplemented with histidine (20 μg/ml) and incubated at 30° C. to form a colonie (in order to confirm the transformant requiring no leucine). The resulting cells are separated from the colonie, inoculated into BurkHolder minimal medium supplemented with histidine (20 μg/ml) and incubated at 30° C. After about 24 hours, the cells in logarithmic growth phase are collected by centrifugation, suspended in a minimal medium (10 ml) containing no phosphoric acid (which is prepared by replacing KH₂PO₄ in BurkHolder minimal medium with KCl, followed by supplementing with 20 μg/ml histidine) in a cell concentration of about 4×10⁶ cells/ml. After incubating at 30° C. for about 24 hours, the culture broth is centrifuged at 4,000 r.p.m. for 10 minutes to collect the cells. The cells thus separated are suspended in a solution (3 ml) of 1.2M sorbitol, 50 mM phosphate buffer (pH 7.2), 14 mM 2-mercaptoethanol and 100 μg/ml Zymolyase-60,000 (manufactured by Seikagaku Kogyo K.K., Japan), and the mixture is gently shaken at 30° C. for 30 minutes to give spheroplast. The spheroplast is collected by centrifugation and is well suspended in a solution (1 ml) of 0.1% tritone X-100 and 50 mM phosphate buffer (pH 7.2), stirred vigorously and then centrifuged at 7,000 r.p.m. for 10 minutes, and the resulting supernatant is taken as the yeast-lysed solution.

The lysed solution (20 μl) obtained above is tested with HBs antigen RIA kit (manufactured by Abbott, U.S.A.) in terms of the HBs antigen activity. The results are shown in Table 1.

TABLE 1

| Clone No. | Host | Plasmid | HBsAg activity (cpm) |
|---|---|---|---|
| 1 | S. cerevisiae AH22 (FERM BP-312) | pAH 201 | 10,597 |
| 2 | S. cerevisiae AH22 (FERM BP-312) | pAH 203 | 13,008 |
| 3 | S. cervisiae AH22 (FERM BP-312) | pAH 205 | 5,548 |
| 4 | S. cerevisiae AH22 (FERM BP-312) | pAS 101 | 11,200 |
| Reference | S. cervisiae AH22 (FERM BP-312) | pAM 82* | 320 |

*This vector has no HBV or HBs gene and is used as a negative reference. (The negative control of RIA kit has an activity of 310 cpm, and the positive control thereof has that of 17,500 cpm)

As to the yeast lysed solution (obtained above from S. cerevisiae AH22/pAH 203), the reactivity and amount of antigen are assumed in accordance with a parallel line assay using a kit for detecting HBsAg as above (cf. Finney, D. J., 1964, "Statistical method in biological assay", 2nd edition, Griffin, London), wherein purified HBsAg obtained from human blood serum is used as a control antigen. The results are shown in the accompanying FIG. 6. As is clear from FIG. 6, the amount of antigen in the culture liquid of the transformed mouse cells is comparatively high such as 2 μg/ml. Moreover, from based on the parallelism with the control antigen, it is also clear that the HBsAg produced by the present invention has similar reactivities (antigenicity, immunogenicity, etc.) to those of HBsAg present in human blood plasma.

The lysed solution obtained above (each 0.4 ml) was subcutaneously inoculated to guinea pigs (female, 300-380 g, 10 animals) once a week for three weeks, and the antibody in blood plasma was determined with a kit for detecting anti-HBs antibody (AUSAB, manufactured by Abbott, U.S.A.). As a result, there was observed in all animals the anti-HBs antibody.

Thus, the preparation of the host vector and HBs antigen therefrom of the present invention is very useful for production of an antigen against Hepatitis B-inducing substance (Dane particles), and HBs antigen prepared by the present invention is useful for the preparation of HBV vaccine and diagnostic reagents.

What is claimed is:

1. A recombinant plasmid for use in the production of Hepatitis B virus surface antigen, which comprises a plasmid vector containing DNA sequences of Saccharomyces cervisiae yeast DNA sequences originated from Escherichia coli plasmid pBR322 and DNA sequences encoding Hepatitis B virus surface antigen, said yeast sequences comprising ars 1, 2μ ori and a marker gene for a transformed yeast in which the marker gene is selected from genes coding for leucine, histidine, tryptophane, uracil and adenine, said sequences from the E. coli plasmid being of about 3.7 kb and including a marker gene for a transformed E. coli in which the marker gene is selected from genes coding for antibiotic resistances against ampicillin, kanamycin, tetracycline and chloramphenicol, said plasmid further comprising the expression control region of the repressible acid phosphatase gene of yeast being a gene for a polypeptide of 60,000 daltons constituting the phosphatase in which the entire phosphatase structural gene of 82 bp and a region in the range of from +1 (ATG) to −100 bp upstream of the phosphatase structural gene are deleted, said DNA sequences encoding Hepatitis B virus surface antigen comprising a fragment of 1.3 kb containing the gene for the 226 amino acids of Hepatitis B virus surface antigen of the subtype adr.

2. The recombinant plasmid according to claim 1, wherein the region to be deleted upstream of the phosphatase structural gene is in the range of from +1 to −50 bp.

* * * * *

UNITED STATES PATENT AND TRADEMARK OFFICE
CERTIFICATE OF CORRECTION

PATENT NO. : 4,778,761

DATED : October 18, 1988

INVENTOR(S) : Atsushi MIYANOHARA et al.

It is certified that error appears in the above-identified patent and that said Letters Patent is hereby corrected as shown below:

On the title page:

Item [73] Assignee: Before "Juridical" insert --Science and Technology Agency, Minister's Secretariat, Director of Finance Division, Tokyo, Japan and the--.

Signed and Sealed this

Eighteenth Day of June, 1991

Attest:

HARRY F. MANBECK, JR.

*Attesting Officer*       *Commissioner of Patents and Trademarks*